(12) United States Patent
Stewart et al.

(10) Patent No.: US 10,039,467 B2
(45) Date of Patent: Aug. 7, 2018

(54) ELECTROPHYSIOLOGY CATHETER DESIGN

(71) Applicant: Medtronic Ablation Frontiers LLC, Minneapolis, MN (US)

(72) Inventors: Mark T. Stewart, Lino Lakes, MN (US); Mark Allen Benscoter, Dellwood, MN (US); Jon Virgil Evans, Eden Prairie, MN (US); Timothy G. Laske, Shoreview, MN (US); Gonzalo Martinez, Mendota Heights, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 69 days.

(21) Appl. No.: 15/164,445

(22) Filed: May 25, 2016

(65) Prior Publication Data
US 2016/0262831 A1 Sep. 15, 2016

Related U.S. Application Data

(62) Division of application No. 13/750,133, filed on Jan. 25, 2013, now Pat. No. 9,370,311.
(Continued)

(51) Int. Cl.
*A61B 5/042* (2006.01)
*A61B 18/14* (2006.01)
(Continued)

(52) U.S. Cl.
CPC ............ *A61B 5/042* (2013.01); *A61B 5/0422* (2013.01); *A61B 18/14* (2013.01);
(Continued)

(58) Field of Classification Search
CPC ................ A61B 18/14; A61B 18/1492; A61B 2018/00071; A61B 2018/00351;
(Continued)

(56) References Cited

U.S. PATENT DOCUMENTS 3,769,984 A 11/1973 Muench
4,010,759 A 3/1977 Boer
(Continued)

FOREIGN PATENT DOCUMENTS

EP 1169972 A1 1/2002
EP 1839581 A1 10/2007
(Continued)

OTHER PUBLICATIONS

International Search Report and Written Opinion dated Dec. 2, 2013 for International Application Serial No. PCT/US2013/054891, International Filing Date: Aug. 14, 2013 consisting of 11 pages.
(Continued)

*Primary Examiner* — Lee S Cohen
(74) *Attorney, Agent, or Firm* — Christopher & Weisberg, P.A.

(57) ABSTRACT

The present invention relates to a method, device, and system for improved mapping and/or ablation of a tissue. The device may generally include an elongate body and a distal assembly affixed to the elongate body that includes a treatment electrode having a conductive mapping region and a selectively conductive ablation region that is conductive of high-frequency current and substantially non-conductive of low-frequency current. Alternatively, the device may generally include a treatment electrode having a conductive mapping or ablation region and a region that is coated with an electrically insulated but thermally conductive layer.

20 Claims, 11 Drawing Sheets

Related U.S. Application Data

(60) Provisional application No. 61/684,385, filed on Aug. 17, 2012, provisional application No. 61/727,163, filed on Nov. 16, 2012.

(51) Int. Cl.
*H01R 43/24* (2006.01)
*H05K 13/00* (2006.01)
*A61B 18/18* (2006.01)
*A61L 29/02* (2006.01)
*A61B 18/00* (2006.01)

(52) U.S. Cl.
CPC .......... *A61B 18/1492* (2013.01); *A61B 18/18* (2013.01); *A61L 29/02* (2013.01); *H01R 43/24* (2013.01); *H05K 13/0046* (2013.01); *A61B 2018/0016* (2013.01); *A61B 2018/00029* (2013.01); *A61B 2018/00071* (2013.01); *A61B 2018/00083* (2013.01); *A61B 2018/00095* (2013.01); *A61B 2018/00107* (2013.01); *A61B 2018/00351* (2013.01); *A61B 2018/00577* (2013.01); *A61B 2018/00642* (2013.01); *A61B 2018/00839* (2013.01); *A61B 2018/1407* (2013.01); *A61B 2018/147* (2013.01); *A61B 2018/1435* (2013.01); *A61B 2018/1467* (2013.01); *A61B 2018/1497* (2013.01); *Y10T 29/49172* (2015.01); *Y10T 29/49176* (2015.01)

(58) Field of Classification Search
CPC .. A61B 2018/00107; A61B 2018/1467; A61B 2018/1497; A61B 5/042; A61B 5/0422
See application file for complete search history.

(56) References Cited

U.S. PATENT DOCUMENTS

| | | | |
|---|---|---|---|
| 4,660,571 A | 4/1987 | Hess et al. | |
| 5,230,349 A | 7/1993 | Langberg | |
| 5,281,213 A * | 1/1994 | Milder | A61B 18/02 606/15 |
| 5,330,471 A | 7/1994 | Eggers | |
| 5,545,161 A | 8/1996 | Imran | |
| 5,833,714 A | 11/1998 | Loeb | |
| 5,849,031 A | 12/1998 | Martinez et al. | |
| 5,913,854 A | 6/1999 | Maguire et al. | |
| 6,090,104 A | 7/2000 | Webster, Jr. | |
| 6,107,699 A | 8/2000 | Swanson | |
| 6,405,733 B1 | 6/2002 | Fogarty et al. | |
| 6,477,396 B1 | 11/2002 | Mest et al. | |
| 6,522,930 B1 | 2/2003 | Schaer et al. | |
| 7,174,219 B2 | 2/2007 | Wahlstrand et al. | |
| 8,449,537 B2 | 5/2013 | Cao et al. | |
| 8,565,851 B2 | 10/2013 | Lau et al. | |
| 9,370,311 B2 * | 6/2016 | Stewart | H05K 13/0046 |
| 2002/0095202 A1 | 7/2002 | Schmidt | |
| 2004/0064175 A1 | 4/2004 | Lessar et al. | |
| 2004/0162554 A1 | 8/2004 | Lee et al. | |
| 2004/0225286 A1 | 11/2004 | Elliott | |
| 2005/0033137 A1 | 2/2005 | Oral et al. | |
| 2005/0059963 A1 | 3/2005 | Phan et al. | |
| 2006/0025757 A1 | 2/2006 | Heim | |
| 2006/0293653 A1 | 12/2006 | Van Wyk | |
| 2006/0293654 A1 | 12/2006 | Morrison et al. | |
| 2007/0005051 A1 | 1/2007 | Kampa | |
| 2007/0005053 A1 | 1/2007 | Dando | |
| 2007/0016185 A1 | 1/2007 | Tullis et al. | |
| 2007/0027448 A1 | 2/2007 | Paul et al. | |
| 2010/0305675 A1 | 12/2010 | Laske et al. | |
| 2011/0028820 A1 | 2/2011 | Lau et al. | |

FOREIGN PATENT DOCUMENTS

| | | |
|---|---|---|
| WO | 2005086683 A2 | 9/2005 |
| WO | 2009089415 A1 | 7/2009 |

OTHER PUBLICATIONS

International Search Report and Written Opinion dated Jan. 27, 2014 for International Application Serial No. PCT/US2013/051972, International Filing Date: Jul. 25, 2013 consisting of 10 pages.

\* cited by examiner

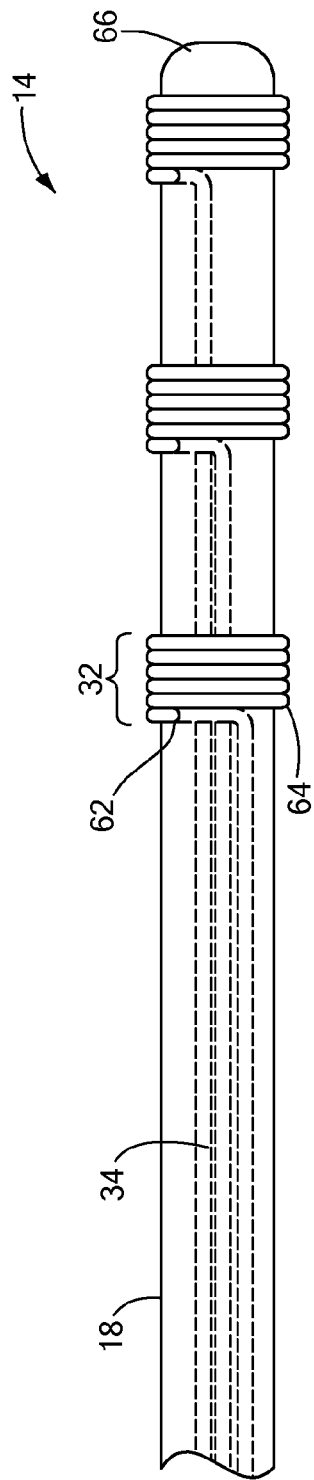
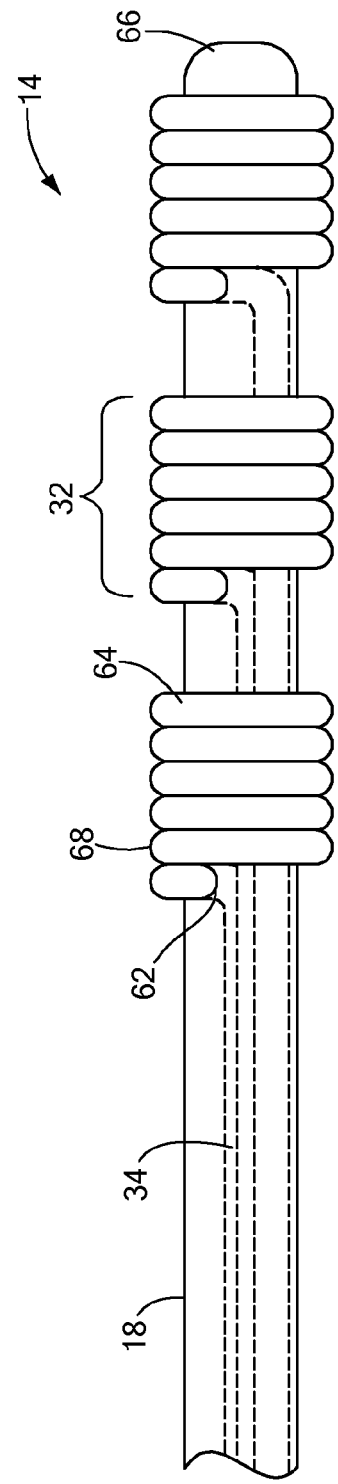
FIG. 6A
FIG. 6B

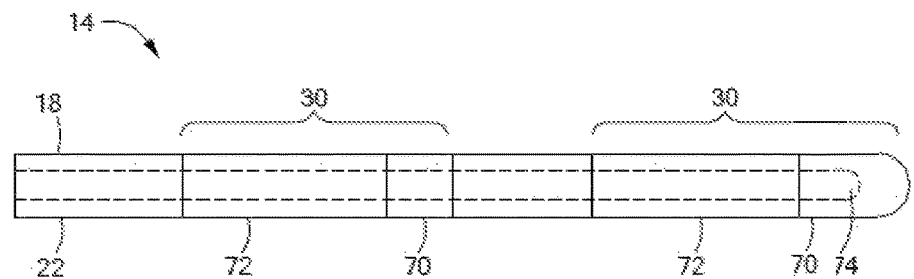
*FIG. 7A*
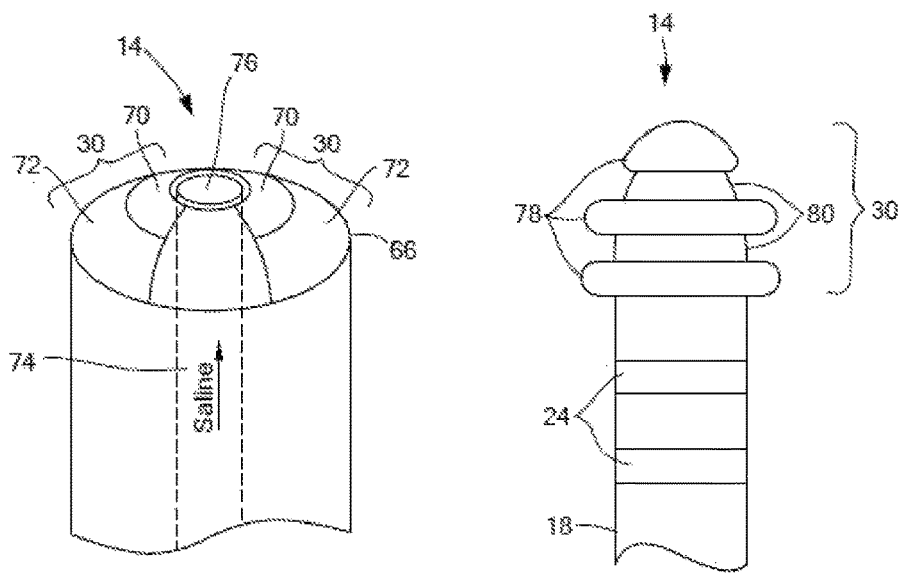
*FIG. 7B*          *FIG. 8*

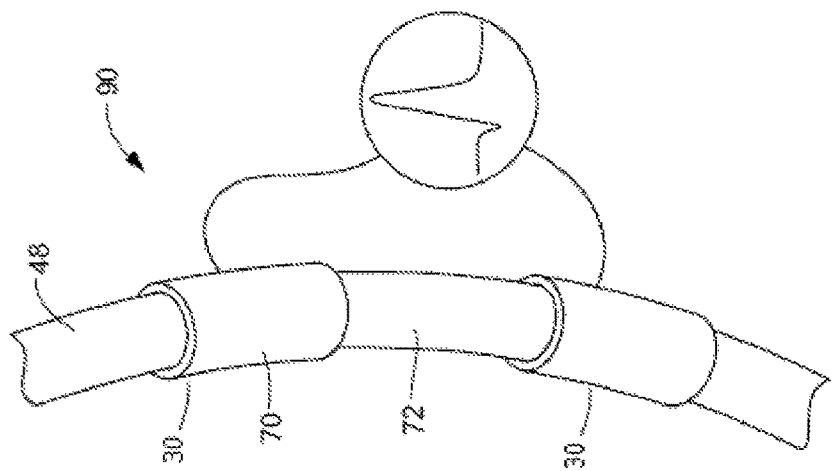
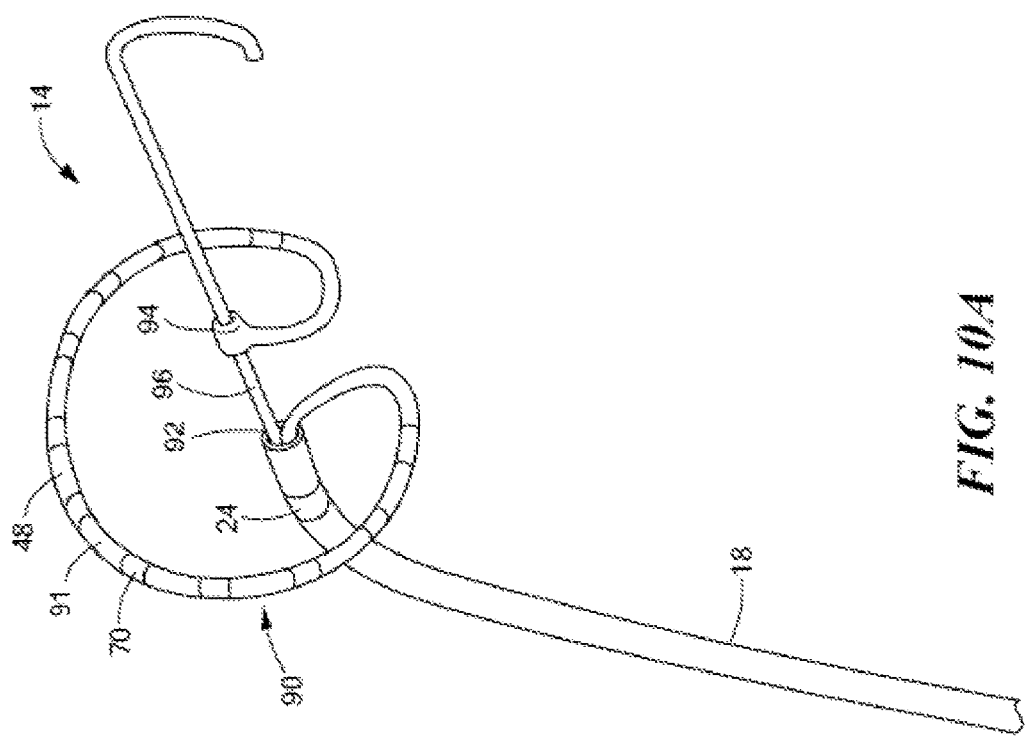
FIG. 10B
FIG. 10A

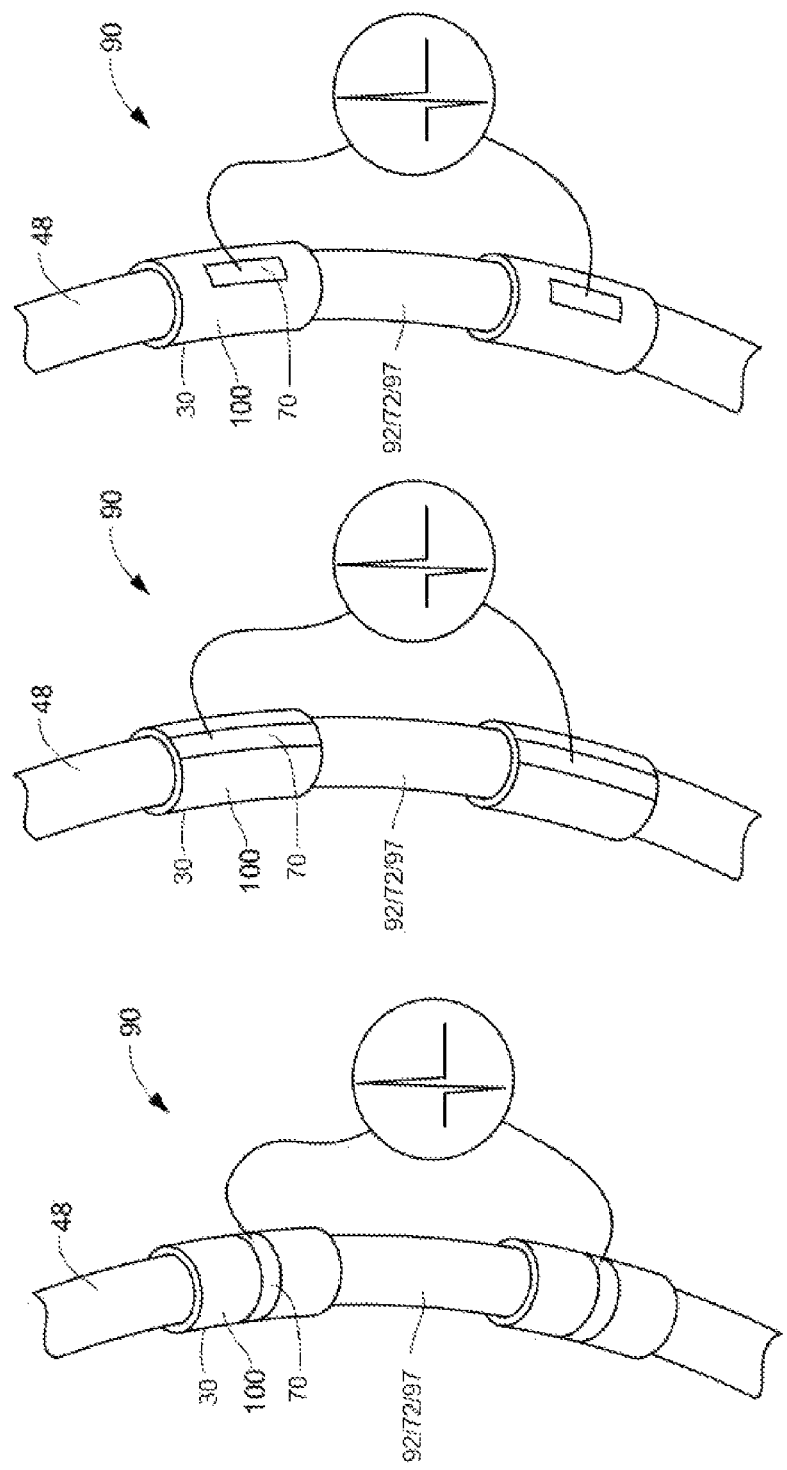

ELECTROPHYSIOLOGY CATHETER DESIGN

CROSS-REFERENCE TO RELATED APPLICATION

This application is a divisional of patent application Ser. No. 13/750,133, filed Jan. 25, 2013, now U.S. Pat. No. 9,370,311, entitled ELECTROPHYSIOLOGY CATHETER DESIGN, which is related to and claims the benefit of U.S. Provisional Patent Application Ser. No. 61/684,385, filed Aug. 17, 2012, entitled MONOPHASIC ACTION POTENTIAL CATHETER DESIGN, and is related to and claims the benefit of U.S. Provisional Patent Application Ser. No. 61/727,163, filed Nov. 16, 2012, entitled MONO-PHASIC ACTION POTENTIAL ELECTROGRAM CATHETER, the entirety of which all is incorporated herein by reference.

STATEMENT REGARDING FEDERALLY SPONSORED RESEARCH OR DEVELOPMENT n/a

FIELD OF THE INVENTION

The present invention relates to a device and system for improved mapping and tissue ablation that may be manufactured at a reduced cost and complexity.

BACKGROUND OF THE INVENTION

Medical procedures are available for treatment of a variety of cardiovascular conditions, such as cardiac arrhythmias, atrial fibrillation, and other irregularities in the transmission of electrical impulses through the heart. As an alternative to open-heart surgery, many medical procedures are performed using minimally invasive surgical techniques, where one or more slender implements are inserted through one or more small incisions into a patient's body. Such procedures may involve the use of catheters or probes having multiple sensors, electrodes, or other measurement and treatment components to treat the diseased area of the heart, vasculature, or other tissue. Minimally-invasive devices are desirable for various medical and surgical applications because they allow for shorter patient recovery times compared to surgery, and for precise treatment of localized discrete tissues that are otherwise difficult to access. For example, catheters may be easily inserted and navigated through the blood vessels and arteries, allowing non-invasive access to areas of the body with relatively little trauma, while other minimally-invasive probes or instruments may be inserted into small openings and directed through targeted anatomy without significant impact or disruption to surrounding tissue.

One such example of a minimally invasive therapy involves the treatment of cardiac arrhythmias or irregular heartbeats in which physicians employ specialized cardiac assessment and treatment devices, such as a mapping and/or ablation catheter, to gain access to interior regions of a patient's body. Such devices may include tip electrodes or other ablating elements to create lesions or other anatomical effects that disrupt or block electrical pathways through the targeted tissue. In the treatment of cardiac arrhythmias, a specific area of cardiac tissue having aberrant electrical activity (e.g. focal trigger, slow conduction, excessively rapid repolarization, fractionated electrogram, etc.) is typically identified first before subsequent treatment. This localization or identification can include obtaining unipolar or bipolar electrograms, or monophasic action potential ("MAP") electrograms of a particular cardiac region. Monophasic action potential recordings document the onset of local tissue depolarization, during repolarization, and the general action potential morphology. The MAP signal is generated by measurement between two electrodes, the first being in contact with the blood but generally not in contact with the myocardium, and the second being in contact with the myocardium, with high enough local pressure to depolarize the underlying myocytes. This increased local pressure preferably is created by a relatively prominent, yet small surface area electrode in stable contact with the myocardium.

MAP signals may be obtained by temporarily depolarizing selected tissue, with responsive electrical activity being recorded or otherwise monitored for an indication of local depolarization timing, refractory period duration, and any aberrant electrical activity. After mapping and diagnosing aberrant tissue, a physician may decide to treat the patient by ablating the tissue. Accurate mapping of the cardiac tissue using bipolar, unipolar, or MAP electrogram signals can reduce the number of ablations necessary to treat an aberrant electrical pathway, and can make the executed ablations more effective. In addition, MAP recordings can substantially improve the ability to determine the timing of local tissue activation which is often ambiguous when recorded using standard intracardiac electrodes.

The accuracy of MAP signal measurement largely depends on quality of contact between one or more mapping electrodes and the heart tissue. For example, motion artifacts caused by a beating heart and nonuniform ventricular contraction can significantly distort detected MAP signals, as movement of the heart will vary the pressure of (and therefore alter the contact between) the mapping electrodes on the heart tissue as well as resulting in unstable sliding contact of the electrodes. Currently known diagnostic cardiac electrophysiology catheters do not accurately and reliably detect MAP signals.

Further, combination mapping and ablation devices reduce procedure time and complexity by eliminating the need to employ separate mapping and ablation devices for each task. Combination mapping and ablation devices also increase ablation accuracy, because once aberrant tissue (the "target tissue") is found, ablation can begin immediately without having to remove the mapping device and relocate the target tissue with the ablation device. It is desirable to include one or more larger electrodes for radiofrequency (RF) ablation, so the large electrode area can provide a large surface area for dissipation into the blood pool of heat absorbed from the tissues. When smaller electrodes, and therefore a smaller active surface area, are used, the electrodes are more likely to incur local overheating, which can lead to thermal denaturation of blood proteins, producing adherent or embolic coagulum or other undesirable effects downstream of the electrodes and the treatment site. Conversely, more accurate electrograms and MAP recordings may be obtained with smaller mapping electrodes.

To provide more effective and efficient medical treatments, it is thus desirable to optimize the apparatus and method of use to ensure more uniform contact between a mapping device and cardiac tissue when recording MAP signals. It is also desirable to have a catheter that can both record monophasic action potentials, and subsequently ablate the local tissue if desired. It is further desirable to provide a mapping apparatus that is simple and cost effective to manufacture.

SUMMARY OF THE INVENTION

The present invention relates to a method, device, and system for improved mapping and/or ablation of a target tissue region, while reducing manufacturing cost and complexity. In a first embodiment, the device may generally include an elongate body and a distal assembly affixed to the elongate body and including a treatment electrode having a first surface, a conductive mapping region, and a selectively conductive ablation region. The selectively conductive ablation region may be conductive of high-frequency current and substantially non-conductive of low-frequency current. The treatment electrode may be composed of metal, such as platinum, platinum alloys, gold, gold alloys, gold with a coating of tantalum, copper with a coating of tantalum, aluminum, tungsten, titanium, tantalum, hafnium, niobium, silver, zirconium, and combinations thereof. The selectively conductive ablative region may include an oxide layer on the treatment electrode first surface. For example, the treatment electrode may be composed of gold and the selectively conductive ablative region may include a layer of oxidized tantalum. Further, the selectively conductive ablative region may be larger than the conductive mapping region. In another embodiment, the treatment electrode may include a coiled region that is prominent from the elongate body, for example, treatment electrode may be a coiled hyptotube electrode. The perimeter of the hyptotube electrode may include one or more substantially angular bends and/or one or more protuberances to further enhance local small area contact pressure with tissue. In another embodiment, the device may include two treatment electrodes, each treatment electrode being substantially disposed about a circumference of the elongate body, the conductive mapping regions of the treatment electrode being coaxial with the longitudinal axis of the elongate body, and the conductive mapping region of each treatment electrode being distal of the selectively conductive ablation region of each electrode. In another embodiment, the elongate body of the device may define a distal region, and the device may further comprise two or more treatment electrodes, each treatment electrode being substantially disposed within a discrete circular sector of the distal tip.

In another embodiment, the device may include an elongate body defining a distal portion, a proximal portion, and a longitudinal axis, and an assembly affixed to the distal portion of the elongate body and defining an anterior face lying in a plane that is substantially orthogonal to the longitudinal axis of the elongate body, the assembly including a plurality of electrodes, each electrode having a first surface, an electrically conductive mapping region, and a thermally conductive and electrically insulated region. The assembly may be a carrier arm, and the electrically conductive mapping region of the mapping electrode may be positioned on the anterior face of the curved carrier arm. The device may further include two carrier arms, the anterior faces of the carrier arms being coplanar and perpendicular to each other. The thermally conductive and electrically insulated region may include a layer of at least one of pyrolytic graphite, graphite, graphene, diamond, diamond-like carbon (DLC) coating, alumina, sapphire, zirconia, tantala, titania, beryllium oxide, polymer composites containing thermally conductive particles, nanoparticles, self-assembling nanoparticles, nanomaterials and composites, olive oil, medical grade silicone oil, and combinations thereof on the first surface. Further, the thermally conductive and electrically insulated region may be composed of gold or gold alloy, and may include a layer of at least one of pyrolytic graphite, graphite, graphene, diamond, diamond-like carbon coating, alumina, sapphire, zirconia, tantala, titania, beryllium oxide, polymer composites containing thermally conductive particles, nanoparticles, self-assembling nanoparticles, nanomaterials and composites, olive oil, medical grade silicone oil, and combinations thereof on the first surface.

In another embodiment, the device may include an elongate body defining a distal portion and a proximal portion, and an assembly affixed to the distal portion of the elongate body and including a plurality of conductive protuberant metal electrode portions and a plurality of substantially insulated portions. Each of the plurality of protuberant electrode portions and plurality of substantially insulated portions may circumscribe the distal assembly housing, and the distalmost electrode portion may have the smallest circumference, and the proximalmost electrode portion has a largest circumference, of the plurality of electrode portions. Further, the plurality of protuberant electrode portions may be alternated with the plurality of substantially insulated portions. The plurality of protuberant metal electrode portions and the plurality of substantially insulated portions may be composed of a metal selected from the group consisting of platinum, platinum alloys, gold, gold alloys, gold with a coating of tantalum, copper with a coating of tantalum, copper with a coating of gold, aluminum, tungsten, titanium, tantalum, hafnium, niobium, zirconium, and mixtures thereof, and each of the plurality of substantially insulated portions includes an outer layer of oxidized aluminum, tungsten, titanium, tantalum, hafnium, niobium, zirconium, and mixtures thereof.

The method may generally include providing a device including a distal assembly comprising one or more conductive regions and one or more selectively conductive regions, the one or more conductive regions and one or more selectively conductive regions being in electrical communication with a high-frequency energy source, and the one or more selectively conductive regions being conductive of conductive of high-frequency energy and substantially non-conductive of low-frequency electric current, positioning the distal assembly in contact with an area of target tissue, recording at least one electrogram from the area of target tissue with the conductive region of the distal assembly, determining whether the at least one electrogram indicates the presence of an aberrant electrical pathway within the area of target tissue, and when the presence of an aberrant electrical pathway within the area of target tissue is indicated, transmitting a high-frequency energy to the conductive region and the selectively conductive region, the conductive region and selectively conductive region ablating at least a portion of the area of target tissue. For example, the high-frequency energy may be radiofrequency energy.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 6A shows a second embodiment of a distal assembly;
FIG. 6B shows a third embodiment of a distal assembly;
FIG. 7A shows a fourth embodiment of a distal assembly;
FIG. 7B shows a fifth embodiment of a distal assembly;
FIG. 8 shows a sixth embodiment of a distal assembly;
FIG. 10A-10H show various configurations of a tenth embodiment of a distal assembly.

DETAILED DESCRIPTION OF THE INVENTION

Figure 9A:
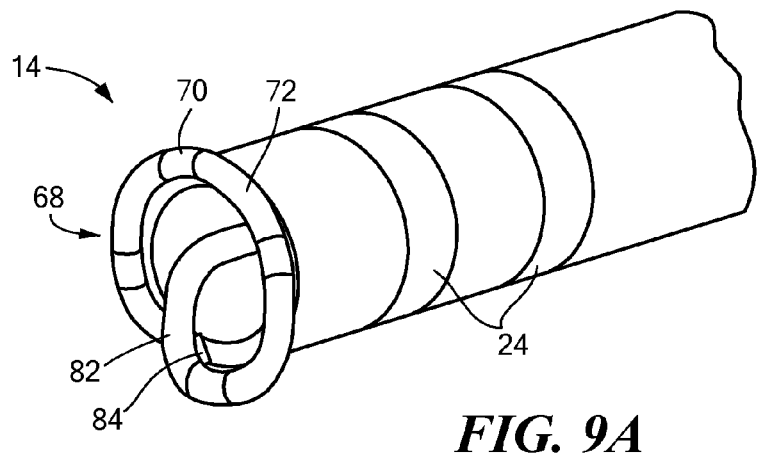
FIG. 9A shows a seventh embodiment of a distal assembly.

As used herein, the term "distal assembly" refers to a distal portion of a medical device that has mapping and/or ablation functionality. If the medical device includes an elongate body, at least a portion of the distal assembly may be distal of the elongate body (for example, as shown in FIGS. 9A-10), or the distal assembly may be substantially affixed on, disposed about, or integral to the distal portion of the medical device (for example, as shown in FIGS. 2 and 6A-7B).

As used herein, the term "selectively conductive metal" refers to a metal with an oxide form or coating that behaves like a capacitor, passing high-frequency currents and pulsed energy but blocking transmission of direct current and low-frequency signals. The metal, for example, aluminum, tungsten, titanium, tantalum, hafnium, niobium, zirconium (and alloys thereof), as well as gold or copper with a thin film of tantalum, or copper with a thin film of gold, may be fully electrically conductive. The oxide of that metal, on the other hand, may have low resistance to high-frequency current flow, thus being selectively conductive, and a high resistance to low-frequency or direct current flow, thus having selectively insulative properties.

Figure 1:
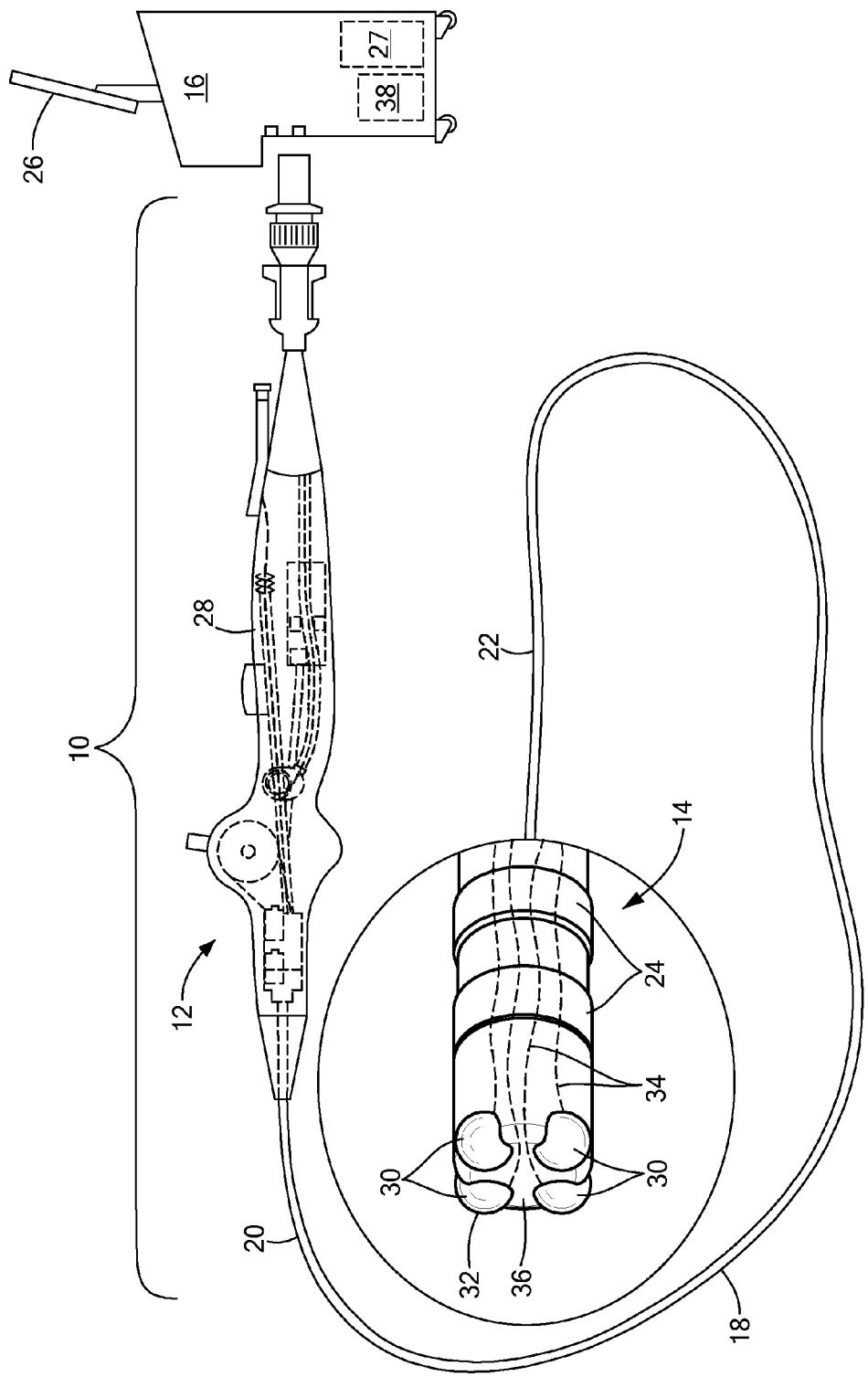
FIG. 1 shows a medical system including a catheter having a distal assembly.

Referring now to FIG. 1, a medical system 10 including a catheter 12 having a distal assembly 14 is shown. The system 10 may generally include a medical device 12 (such as a catheter or surgical probe) coupled to a console 16 or other operating equipment. The catheter 12 has a distal assembly 14 positionable at or near a target tissue region. The catheter 12 may have an elongate body or catheter shaft 18 with a proximal portion 20, a distal portion 22, and may define a lumen therebetween (not shown in FIG. 1). The distal portion 22 of the elongate body 18 may include one or more reference electrodes 24 in electrical communication with the distal assembly 14 and console 16. The console 16 may include one or more computers 26 for storing data, interpreting signals received from the device (for example, determining whether received signals indicate an aberrant electrical activity within a patient's heart), generating alerts, controlling the system, and the like, and may also include one or more fluid reservoirs 27, vacuums, power sources, and the like. The elongate body 18 may be both flexible and resilient, with sufficient column strength and torsional rigidity facilitating steady contact with tissue to improve signal fidelity in mapping contacted tissue. The catheter 12 may also have a handle 28 affixed to the proximal portion 20 of the elongate body, which may include one or more fluid inlet and outlet ports, actuators, connectors, and other control and/or connecting elements.

The distal assembly 14 is coupled to the distal portion 22 of the elongate body 18, and includes one or more mapping and/or ablation electrodes 30, each comprising an electrode head 32 and electrode wire 34. The one or more electrodes 30 may be permanently affixed to an electrode assembly housing 36 (as shown and described in FIGS. 2-5). The distal assembly 14 may be operable at least for mapping a target tissue region, but may also be operable as a treatment assembly. For example, the console 16 may include a radio frequency (RF) generator or high voltage pulsed energy generator 38 in electrical communication with one or more of the electrodes 30 or the electrode assembly housing 36 such that the distal assembly 14 may also be used to ablate or electroporate a target tissue region. The catheter 12 and system 10 may be configured for use with any of a variety of energy modalities, including cryoablation, RF ablation, and electroporation. Further, the catheter 12 and system 10 may be configured for mapping tissue, for example, recording and processing electrograms from cardiac tissue.

Referring generally to FIGS. 2-10, embodiments of the distal assembly 14 and methods for manufacturing are shown and described. In all embodiments, the distal assembly 14 offers a cost effective and quality performance advantage over currently known devices. For example, although all embodiments may provide more accurate mapping, the distal assembly 14 of FIG. 2 may offer combined mapping and ablation functionality in a space-saving configuration with fewer components and manufacturing steps, whereas the distal assemblies 14 of FIGS. 6A, 6B, and 8-10 may further offer the advantage of having combined functionality without the need for creating each component from a different material. Further, the distal assembly 14 of FIGS. 8-10 may offer the advantage of including features that enhance contact between mapping electrodes and tissue. Finally, the distal assemblies 14 of FIGS. 7A and 7B may offer the advantage of including a single electrode that has both mapping and ablation functionality.

The distal assemblies 14 of FIGS. 2-10 may include components (for example, mapping and/or electrodes and/or a housing assembly) that are composed of a selectively conductive material. Metal oxides such as tantalum pentoxide may be referred to as "selectively conductive metals." Tantalum pentoxide, for example, is selectively conductive. That is, it has the unique ability to block direct current (DC) while allowing high-frequency current conduction (such as radiofrequency energy). Tantalum pentoxide passes high-frequency current preferentially but blocks DC transmission. Metals such as tantalum, aluminum, tungsten, titanium, haffnium, niobium, zirconium, and mixtures thereof, which have oxides that are selectively conductive. Additionally, doped semiconductors such as p-type and n-type doped silicon and gallium, and composite materials made from ceramics as well as conductive polymers, metal-polymers, metal-ceramic composites, and some nanomaterials may also be selectively conductive. Further, tantalum (Ta) and tantalum compounds such as grain-stabilized tantalum (TaKS), tantalum pentoxide (Ta$_2$O$_5$), tantalum-tungsten (TaW), capacitor quality tantalum (TaK), or similar are highly corrosion resistant. Tantalum compounds also display excellent cold ductility, high melting point (for example, Ta has a melting point of 3,017° C.), outstanding resistance against aqueous solutions and metal melts, superconductivity, and a high level of biocompatibility. Further, TaKS, for example, is radiopaque, making it well suited for use in catheters that must be located within and navigated through a patient's body. Tantalum and tantalum compounds can be even more durable than MP35N (a nickel-cobalt-chromium-molybdenum alloy commonly used material for medical implantable devices such as catheter wires that is nonmagnetic, has high tensile strength, good ductility and toughness, and excellent corrosion resistance) and is less expensive than platinum. Additionally, as shown in FIGS. 7A and 7B, the distal assembly 14 may include a single electrode 30, wherein at least a portion of which is composed of a tantalum compound (for example, Ta$_2$O$_5$) and at least a portion of which is composed of a different material (for example, gold, gold alloy, copper coated with gold, or platinum). As a result, the tantalum portion of the electrode may be used to ablate or electroporate tissue using, for example, RF energy (for example, renal, liver, or prostate tissue), whereas the non-tantalum portion of the electrode may be used to deliver a direct current stimulus to or record direct current from the tissue.

Figure 2:
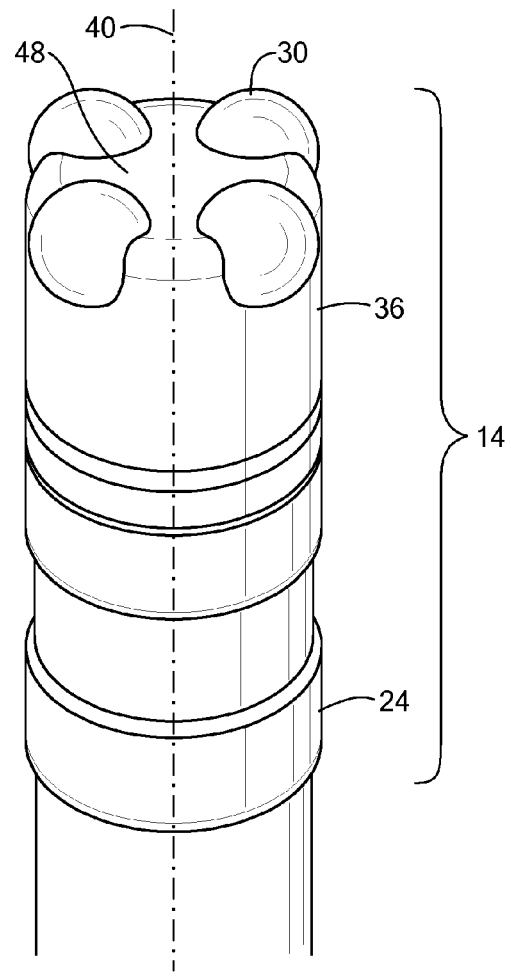
FIG. 2 shows a first embodiment distal assembly.

Referring now to FIG. 2, a first embodiment of a distal assembly 14 is shown. The distal assembly 14 may include a housing 36 and one or more electrodes 30, such as monophasic action potential (MAP) electrodes, each positioned a radial distance from the longitudinal axis 40 of the housing 36. If two electrodes 30 are used, the electrodes 30 may be positioned opposite each other. If three or more electrodes 30 are used (for example, four electrodes are shown in FIG. 2), the electrodes 30 may have a radial symmetry about the housing longitudinal axis 40.

Figure 3:
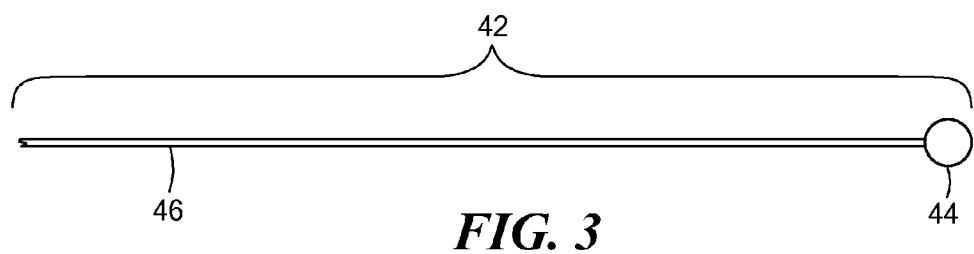
FIG. 3 shows a bulbed wire of the distal assembly of FIG. 2.
Figure 4:
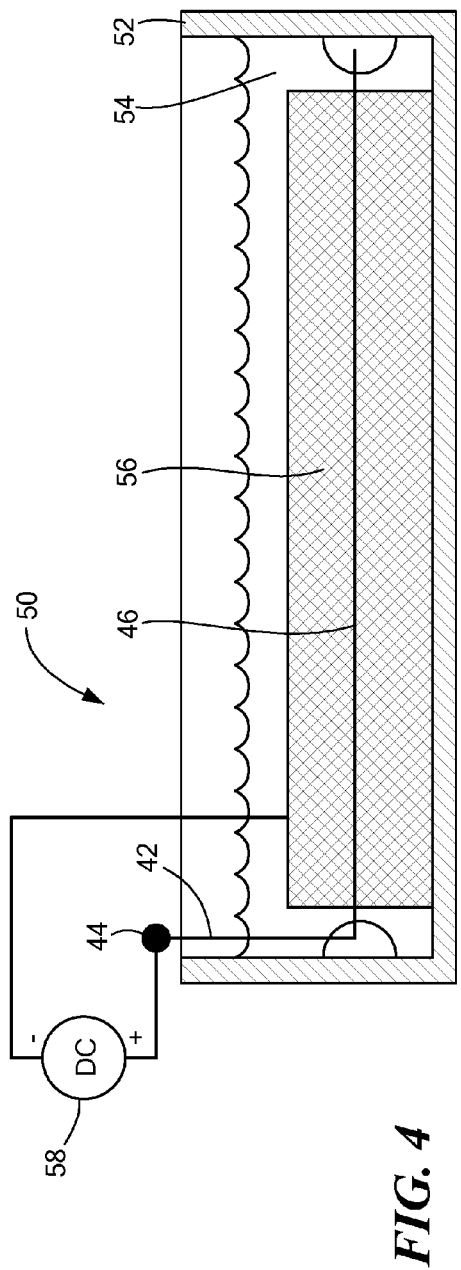
FIG. 4 shows a schematic diagram of an electrochemical cell for use in conjunction with anodizing and annealing bulbed wires, such as forming a tantalum pentoxide layer on a tantalum surface.
Figure 5:
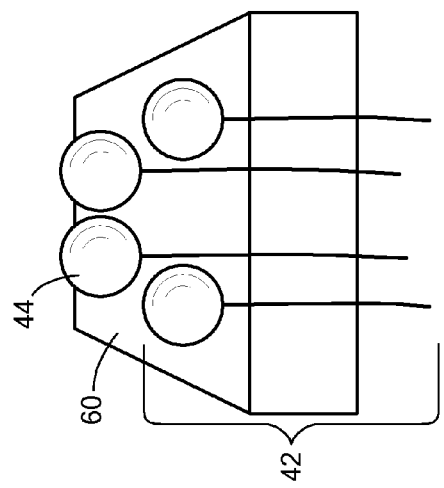
FIG. 5 shows a simplified depiction of a holder adapted to contain bulbed wires for use in conjunction with a process for imparting further corrosion resistance or selective electrical conductivity to the bulbed wires of FIG. 2.

The distal assembly 14 shown in FIG. 2 may have been formed according to the method shown and described in FIGS. 3-5. For example, one or more bulbed wires 42 comprising a bulb portion 44 and a wire portion 46 may be created (as shown and described in FIG. 3). The wire 46 portion of each bulbed wire 42 may then be anodized (as shown and described in FIG. 4), and the bulb portion 44 of each bulbed wire 42 may be composed of the non-anodized material or be electroplated, sputtered, or ion-embedded with a corrosion-resistant material or material having other beneficial properties (as shown and described in FIG. 5).

Once one or more bulbed wires 42 have been treated (for example, anodized and electroplated), the wires 42 may be placed into and bonded to an electrode assembly housing (referred to as the "assembly housing") 36. For example, four bulbed wires 42 may be used. At this stage (that is, when the bulbed wires 42 are seated within the mapping assembly housing 36), the bulbed wires are referred to as electrodes 30, comprising electrode heads 32 and electrode wires 34. In the embodiment shown in FIG. 2, the electrodes 30 and electrode assembly housing 36 are collectively referred to as the distal assembly 14. However, not all embodiments include a housing 36 (for example, the embodiments of FIGS. 6A, 6B, 9, and 10A-10C). The assembly housing 36 includes an anterior face 48 from which the one or more electrode heads 32 may protrude. Alternatively, the electrode heads 32 may be mounted within the assembly housing 36 such that the electrode heads 32 are substantially flush with the anterior face 48 of the electrode housing 36. For example, the assembly housing 36 may include a socket sized to receive each electrode 30 such that the electrode head 32 is seated within the socket and the electrode wire 34 passes through an opening in the socket and into the elongate body, once the housing is coupled to an elongate body. The electrodes 30 may be affixed to the electrode assembly housing 36 using adhesive, thermoplastics, or other known techniques.

The distal assembly 14 of FIGS. 2-5 may be particularly suited for diagnostic purposes, i.e. mapping. However, the distal assembly 14 alternatively may be used as part of a combination ablation and mapping device 12. For example, the assembly housing 36 may be in electrical communication with an energy source (such as RF energy) and composed of an electrically conductive material, or coated or cladded with an electrically conductive material, so that the electrodes 30 may be used for mapping and the housing 36 (which may have a larger "footprint" than the mapping electrodes) may be used for ablation. In this case, a thin insulative layer could be incorporated to electrically isolate the electrode heads 32 from the assembly housing 36. For example, an insulative layer could be disposed within the sockets of the assembly housing 36. Alternatively, the assembly housing 36 and electrodes 30 may be composed of a conductive material, but the housing 36 may include an outer layer of a selectively conductive material. Additionally or alternatively, the assembly housing 36 may be composed of a low-durometer, resilient material such as silicone, a polymer or conductive polymer, air-filled balloon, gel, fiber composite, or the like, that conforms to irregular geometries while ensuring contact between the electrode head 32 and target tissue region. For example, as the heart beats, the deformable housing may absorb the pressure to preserve contact between the electrode head and target tissue region.

Once assembled, the distal assembly 14 may be coupled to the distal portion 22 of the elongate body 18, with the electrode wires 34 providing electrical connection between the distal assembly 14 and catheter 12 and/or system 10. Thus, the entire distal assembly 14 may include as little as two components (for example, if a single electrode and distal assembly housing were used). In a non-limiting embodiment, the distal assembly 14 as shown in FIG. 2 may include six components: four electrodes 30, the assembly housing 36, and a reference electrode 24. The assembly housing 36 and electrodes 30 may be composed of the same material. This embodiment includes fewer components than known mapping assemblies, at least in the electrodes, which reduces cost and assembly time while providing higher reliability.

Referring now to FIG. 3, a bulbed wire 42 of the distal assembly 14 of FIG. 2 is shown. The bulbed wire 42 may be manufactured or molded from a volume of metal such that a bulb 44 or substantially spherical shape is formed at one end (referred to as the "bulb"), such as by cold forming and/or extrusion. The bulb 44 may become the electrode head 32 (as shown and described in, for example, FIGS. 2, 4 and 5), so it may have any dimensions suitable for the final mapping assembly. Having a single-piece electrode head 32 and electrode wire 34 eliminates the need to weld an electrode to a wire. A two-piece system is also feasible, but would increase cost and manufacture time and complexity. The bulbed wire 42 may be composed of a highly corrosion-resistant material, such as tantalum or tantalum compound (such as Ta$_2$O$_5$ or TaKS).

Referring now to FIG. 4, a schematic diagram of an electrochemical cell 50 for use in conjunction with anodizing and annealing bulbed wires 42 is shown. Once the bulbed wire 42 of FIG. 3 is formed, the wire portion 46 may be anodized to create a thin oxide layer on the external surface of the wire portion 46. For example, the insulating layer may be approximately 1 μm thick. During the anodizing process, the wire portion 46 is placed into a container 52 containing an electrolytic solution 54 such as $H_3PO_4$, $H_2SO_4$, ammonium tartrate, or the like. The container 52 may also include a cylindrical mesh electrode 56, and the wire portion 46 to be oxidized may be disposed through the center of the cylindrical mesh electrode 56. The mesh 56 and wire 46 may be coupled to a controllable power source 58. Then, a current (direct, alternating, or pulsed) may be passed through the solution 54, creating an oxide layer about the wire 46. This oxide layer further protects the wire against corrosion and imparts a conductive barrier to electrically isolate the wire from adjacent components and structures. The wire portions 46 of multiple bulbed wires 42 may be anodized at once. Although the entire structure can be anodized, the preferred embodiment anodizes only the regions of the assembly that will be adjacent to other conductive structures to provide an insulative barrier. For example, the wire 46 and bulb 44 may be composed of tantalum, and only the wire 46 may then be anodized to create an oxide layer. This process may be used for components of any of the distal assemblies shown and described herein that include an oxide layer.

Referring now to FIG. 5, a schematic diagram of a holder 60 adapted to contain bulbed wires 42 for use in conjunction with a process for imparting further corrosion resistance to the bulbed wires 42 of FIG. 3 is shown. After being anodized, one or more materials may be deposited on the bulbs 44 to enhance electrical conductivity, provide added corrosion resistance, or impart other beneficial qualities. For example, iridium oxide may be electrodeposited on the bulbs 44 or nickel-titanium alloy may be sputtered onto the bulbs 44. Additionally or alternatively, sputtering may be used to deposit nickel-titanium alloy, gold, gold alloy, platinum or platinum-based alloy, or the like. However, other materials and techniques may be used. For example, the wire 42 may be composed of gold with a tantalum coating. The tantalum coating on the bulb 44 may be etched, and the exposed gold may then be anodized or electroplated, sputtered, or ion-embedded with a coating of platinum-iridium. Prior to treating the bulbs 44 (for example, by electrodeposition or sputtering), one or more bulbed wires 42 may be placed into a holder or container 60 to hold them in place. The holder or container 60 may be adapted to hold any number of wires 42, and may generally hold the wires 42 such that the bulbs 44 are accessible on the top of the holder 60 (as shown in FIG. 3). Once the wires 42 are in place, the bulbs 44 may be treated.

Referring now to FIGS. 6A and 6B, a second and third embodiment of a distal assembly 14 is shown. In both embodiments, the electrode head 32 (the conductive portion) and the electrode wire 34 (the insulated portion) are not only composed of the same material, but are also created from a single piece of material (collectively referred to as an "electrode"). This may reduce manufacturing cost and complexity. Additionally, more than one electrode wires 34 may be used within a catheter body 18 without the need for including insulation material between the wires.

In the embodiment shown in FIG. 6A, a plurality (for example, three) electrode wires 34 are disposed within a medical device, such as a catheter elongate body 18. Each wire 34 may be composed of a metal (for example, tantalum or TaKS) and include an outer insulative oxide layer (for example, tantalum pentoxide). When low-frequency or DC voltage flows through the wire, the wire 34 will function as an insulated conductor of energy. Therefore, no additional insulative material is required within the medical device to electrically insulate each wire 34 from the others. This may not only increase the available space within the medical device for other components such as pull wires, push rods, etc., but may also decrease manufacturing cost and complexity. Each wire 34 may extend through internal portion of the elongate body 18 for a distance, and then exit the wall of the elongate body 18 at an exit point 62. From the exit point 62, the wire 34 may then be disposed about an exterior distal portion in one or more coils 64, which may be referred to as an electrode head 32. Unlike the wire 34, this external coiled portion 64 may not include an oxidative layer, and therefore may be electrically conductive. Further, the coiled portion 64 may have a hydrophilic coating to reduce the likelihood of air collecting within the turns of the coils. The electrodes 30 may be made as shown and described in FIGS. 3-5. Additionally, a housing or at least a portion of a medical device (for example, an elongate body) may be overmolded onto the electrodes to provide a seal at the exit point 62. The distal tip 66 of the elongate body 18 may have an atraumatic rounded or blunt configuration to prevent injury to the patient during mapping and/or ablation procedures.

The embodiment shown in FIG. 6B has substantially the same configuration as the embodiment shown and described in FIG. 6A, except that a hypotube 68 instead of a wire may be used. Like the wire of the embodiment in FIG. 6A, the hypotube 68 may comprise an electrode 30 (conductive portion) and a "wire" 34 (insulated portion); however, unlike the embodiment in FIG. 6A, the hypotube 68 may contain a volume of coolant or saline solution for cooling the electrode 30 portion of the hypotube 68 during ablation procedures (for example, during RF ablation). The conductive portions of both embodiments shown in FIGS. 6A and 6B may be used for mapping and/or ablation. The small diameter hypotube provides increased local tissue contact pressure against the endocardium in any orientation, providing reliable MAP recording capability.

Referring now to FIGS. 7A and 7B, a fourth and fifth embodiment of the distal assembly 14 are shown. These embodiments include an electrode 30 that has both mapping and ablation functionality. As shown in FIG. 7A, one or more electrodes 30 may be disposed about the distal portion 22 of a medical device, such as the flexible, elongate body 18 of a catheter. Although FIG. 7A shows two electrodes 30, any number of electrodes 30 may be used. Each electrode 30 may include a conductive region 70 and a region that is selectively conductive 72. As described herein, the electrode 30 may be composed of a highly conductive metal such as gold and may include a thin film coating of a metal such as tantalum, and the selectively conductive region 72 may include an outer oxide layer, whereas the conductive region 70 does not. The oxide layer may be an oxide of aluminum, tungsten, titanium, tantalum, hafnium, niobium, zirconium (and alloys thereof). The oxide layer in the case of tantalum pentoxide may be between approximately 10 nm and approximately 5000 nm, preferably approximately 100 nm to approximately 1000 nm. Further, the conductive region may have a layer of conductive material such as gold or gold alloy sputtered, ion-embedded, or electrodeposited on an outer surface. The conductive region 70 may have a smaller surface area than the selectively conductive region 72. As a non-limiting example, two electrodes 30 may be positioned on the device distal end such that the conductive regions 70 are each located on the distal end of the electrode 30, and the electrodes 30 are spaced a distance apart by the material of the device (for example, a catheter elongate body), which material provides insulation between electrodes. Further, a fluid lumen 74 may be disposed within the elongate body 18 that is in fluid communication with a source of saline or similar fluid for cooling the electrodes 30. During use, measurement by the electrodes 30 of a low-frequency intracardiac electrogram or direct current voltage will be only from the portions of the electrodes in the conductive region 70, whereas the selectively conductive region 72 is insulated by the oxide layer and does not measure electrograms. As described above, smaller electrodes 30 are less likely to corrode under high voltage and produce more accurate electrograms. Activating the electrodes 30 with high-frequency pulses or RF energy may cause the entire electrode 30, both conductive 70 and selectively conductive regions 72, to function as an ablation electrode having a larger footprint than that of the electrode when the selectively conductive region 72 is insulated during mapping procedures.

The embodiment shown in FIG. 7B generally functions in the same manner as the embodiment shown in FIG. 7A. FIG. 7B, however, shows two electrodes 30 radially arranged about the distal portion 22 of the device (although any number of electrodes may be used). That is, each electrode 30 may be substantially disposed within a discrete circular sector of the distal region 22 of the device, for example, an elongate body 18. The fluid lumen 74 may define an opening 76 at the distal tip 66 of the device, and the conductive region 70 of each electrode 30 may be closest to the lumen opening 76 or distal tip 66 to facilitate mapping when the selectively conductive region 72 is insulated. When the selectively conductive region 72 is conductive, the entirety of each electrode 30 may function as an ablation electrode. In both FIGS. 7A and 7B, the fluid lumen 74 containing saline or similar nontoxic fluid may be open to the environment, and the saline may be allowed to exit the device into the patient's bloodstream through the lumen opening 76. Alternatively, the fluid lumen may be in communication with a source of refrigerant that is expanded to cool the electrodes 30, and that is recovered by a vacuum after it is expanded in the distal portion 22 of the device proximate the electrodes 30.

Referring now to FIG. 8, a sixth embodiment of a distal assembly is shown. The distal assembly 14 may have a generally conical shape, but may include one or more protruding electrode rings 78 (for example three protruding electrode rings 78 are shown in FIG. 8). The protruding electrode rings 78 may have rounded edges to prevent injury to the patient. Between the protruding electrode rings 78 may be one or more recessed insulated portions 80. The protruding electrode rings 78 and recessed insulated portions 80 may be composed of the same material. For example, the protruding electrode rings 78 and recessed insulated portions 80 may be composed of a metal (for example, tantalum), and the recessed insulated portions 80 may have an oxide layer (for example, tantalum pentoxide) or may have a coating of an electrically insulating and thermally conductive material (for example, diamond-like carbon). As a non-limiting example, the oxide layer or the layer of thermally conductive material may be between approximately 10 nm to approximately 5000 nm. The protruding electrode rings 78 may function as mapping electrodes, and the protrusions may enhance contact and establish a higher local pressure between the rings and tissue, thereby enhancing depolarization of the tissue during mapping procedures and providing more reliable and accurate mapping (for example, MAP) signal recording. Additionally, if the insulated portions 80 are composed of a selectively conductive material, both the protruding electrode rings 78 and insulated portions 80 may also be capable of functioning as a single, larger ablation electrode. Alternatively, the insulated portions 80 could be composed of a different material. Even though this may add to manufacturing cost and complexity, the configuration of the distal assembly would still function to produce better mapping signals.

Figure 9B:
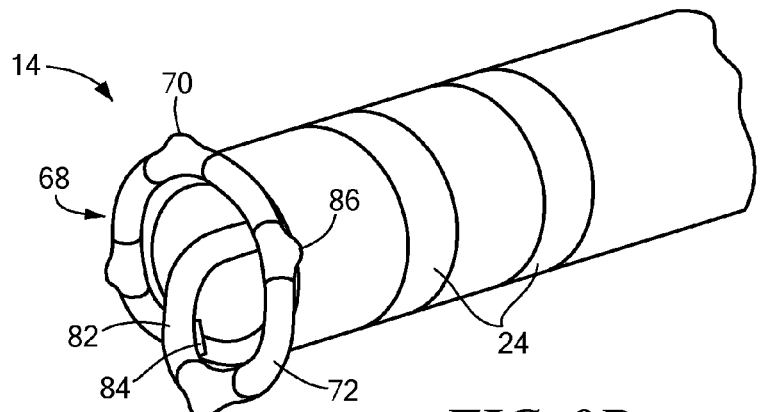
FIG. 9B shows an eighth embodiment of a distal assembly.
Figure 9C:
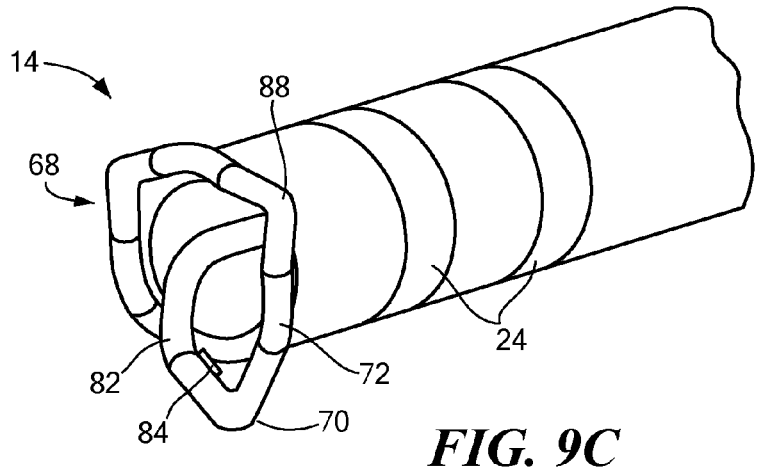
FIG. 9C shows a ninth embodiment of a distal assembly.

Referring now to FIGS. 9A-9C, a seventh, eighth, and ninth embodiment are shown. All three embodiments may include a coiled hypotube electrode 68 disposed about the distal portion 22 of a medical device, such as an elongate body 18 of a mapping and/or ablation catheter. It will be understood that the drawings show only a single winding but additional, more proximal windings may be included in an ablation device. In such embodiments, the proximal windings may be made selectively conductive as described previously. The hypotube 68 in each embodiment may be in fluid communication with a source of saline or similar fluid (as described in FIGS. 7A and 7B), or with a cryogenic fluid, for cooling the hypotube electrode 68. The small diameter hypotube may provide increased local tissue contact pressure against the endocardium in any orientation, providing reliable MAP recording capability. The hypotube 68 may be coiled or wound around the distal portion 22 of the elongate body 18, the hypotube 68 winding at least approximately 360° about the distal portion 22 of the elongate body 18. Alternatively, the hypotube may include a coil or winding 82 that is distal from the elongate body 18 (as shown in FIGS. 9A-9C). Alternatively, the hypotube may include multiple coils or windings 82 that are disposed about the distal portion of the elongate body or that are distal from the elongate body 18. Further, the hypotube 68 of each embodiment may be composed of a metal (for example, tantalum or stainless steel plated with gold or gold alloy) and include one or more alternating selectively conductive regions 72 or more proximal hypotube windings (not shown), having an oxide layer (for example, tantalum pentoxide). As a non-limiting example, the oxide layer may be between approximately 10 nm to approximately 5000 nm, preferably approximately 100 nm to approximately 1000 nm. The exposed (non-oxidized) conductive regions 70 may be smaller (that is, have less surface area) than the oxidized selectively conductive regions 72 to enhance signal quality during mapping when recording intracardiac electrograms. Finally, all embodiments may include one or more thermocouples or thermisters 84 in contact with the hypotube 68 to monitor temperature of the hypotube 68.

The hypotube of FIG. 9A may include a coil 82 that has a substantially smooth circumference without any bumps, ridges, or textures. Conversely, the hypotube 68 of FIG. 9B may include a plurality of elements 86 that are prominent from (or protrude from) a surface of the hypotube 68 to further enhance local small area contact pressure with tissue at the site of contact with each of the prominent elements 86, thus enhancing MAP signal recording capability by increasing local pressure on the tissue under the prominent elements 86. Each prominent element 86 may extend from a surface of the hypotube 68, for example, the outer circumference or perimeter of the hypotube. Although four prominent elements 86 are shown in FIG. 9A, it will be understood that any number of prominent elements 86 may be used to enhance contact between the hypotube 68 and tissue of interest.

Likewise, the hypotube 68 of FIG. 9C may be bent to include one or more substantially angular bends 88. Each bend 88 may be prominent from (or protrude from) the outer circumference of the hypotube 68, thus creating prominent sites about the hypotube 68 to further enhance local small area contact pressure with tissue and improving MAP signal recording capability. Although FIG. 9C shows three protuberant bends 88, it will be understood that any number of bends may be included to enhance MAP signal recording capability when the device is positioned in most any orientation against tissue of interest. Alternatively, the embodiments shown in FIGS. 9A-9C may be made entirely with a conductive surface and without the selectively conductive areas.

Figure 10H:
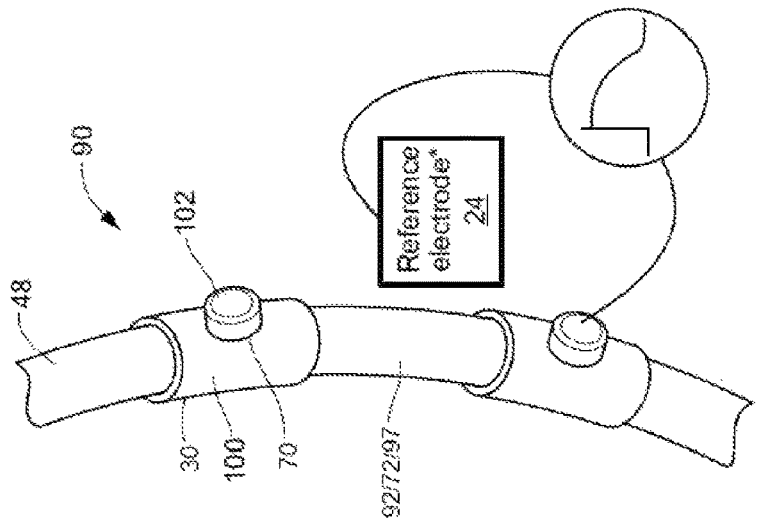

Referring now to FIGS. 10A-10H, various configurations of a tenth embodiment of a distal assembly 14 are shown. The embodiment shown in FIGS. 10A-10H may have the general appearance of a catheter such as the Pulmonary Vein Ablation Catheter (PVAC) sold by Ablation Frontiers (Medtronic Inc., Minneapolis, Minn.), which is an over-the-wire circular mapping and ablation catheter. The PVAC device may include a carrier arm 90 bearing one or more electrodes, typically having either nine or ten electrodes 30. Although FIGS. 10B-10H show and describe only two electrodes 30 on the carrier arm 90, the features of the described electrodes 30 will also apply to any other electrodes 30 included on the carrier arm 90. The electrodes 30 may be conductive, and the carrier arm 90 may be composed of a non-conductive material 91 (as shown in FIG. 10A). Alternatively, the embodiments of FIGS. 10A-10H may not include individual electrodes, but rather a flexible curved carrier arm 90 that is composed of a metal, such as gold, with an electrically insulated but thermally conductive coating (for example, diamond-like carbon) or with a selectively conductive coating (for example, gold with a thin film coating of tantalum that is oxidized to form tantalum pentoxide), with one or more alternating uncoated conductive regions 70. As a non-limiting example, the oxide layer may be between approximately 10 nm to approximately 5000 nm, preferably approximately 100 nm to approximately 1000 nm. The exposed or uncoated conductive regions 70 may be smaller (that is, have less surface area) than the oxidized selectively conductive regions 72 (or electrically insulated but thermally conductive regions) to enhance signal quality during mapping when intracardiac electrogram voltage is measured. Alternatively, the conductive regions 70 and selectively conductive regions 72 may be the same size. As a non-limiting example in which electrodes 30, are borne on the carrier arm 90, the carrier arm 90 may have a diameter of approximately 25 mm, and each of the electrodes 30 and portions of the carrier arm 90 between the electrodes 30 may be approximately 3 mm wide. Further, the carrier arm 90 may include ten electrodes affixed thereto.

A first end 92 of the carrier arm 90 may be affixed to, for example, an elongate body 18 of the device, whereas a second end 94 of the carrier arm 90 may be affixed to a guidewire sheath 96 that is slidably receivable within the device. Therefore, the carrier arm 90 may be transitionable from a substantially linear delivery configuration when the guidewire sheath 96 is extended to a curved treatment configuration when the guidewire sheath 96 is retracted or partially retracted. For example, FIG. 10A shows the guidewire sheath 96 being partially retracted, and the carrier arm 90 extending approximately 360° between the first end 92 and the second end 94 of the carrier arm 90.

FIG. 10B shows a close-up view of a portion of the carrier arm 90, wherein the conductive regions 70 are entirely conductive. The entire carrier arm 90 may be non-conductive or selectively conductive in order to ablate or electroporate tissue when high-frequency or pulsed current is applied (for example, RF voltage). Alternatively, the carrier arm 90 may be electrically insulated and thermally conductive, as described for FIGS. 10C-10H. Further, although FIG. 10B shows electrodes 30 affixed to the carrier arm 90, the electrodes 30 may be integral to the carrier arm 90, as described above in FIG. 10A. In the example shown in FIG. 10B, the conductive electrodes 30 are affixed to the carrier arm 90, and the carrier arm 90 is selectively conductive 72. Further, the conductive 70 electrodes 30 shown in FIG. 10B may wrap all the way around the circumference of a cross section of the carrier arm 90. The figure also shows a portion of an electrogram signal (inset).

FIGS. 10C-10H show close-up views of carrier arm 90 portions wherein the electrodes 30 are partially conductive. That is, the electrodes 30 are conductive only in certain areas, in particular, areas that will be in contact with target tissue (for example, an anterior or tissue-facing surface 48 of the carrier arm 90). For example, the electrodes 30 may be composed of a material, such as gold or gold alloy, that is affixed to the outer surface of the carrier arm 90 (which may be non-conductive 91, selectively conductive 72, or electrically insulated but thermally conductive 97; depicted in the figures as "92/72/97"), and only a portion of the electrode 30 may be uncoated or exposed (that is, conductive). The remaining portions 100 of the electrodes 30 may be selectively conductive (for example, composed of gold with a thin film outer layer of tantalum that has been oxidized to form tantalum pentoxide) or electrically insulated but thermally conductive (for example, having an outer layer of diamond-like carbon). The electrically insulative but thermally conductive outer layer may dissipate heat to the bloodstream yet prevent energy loss to the non-tissue-facing surfaces that are not in tissue contact. The electrically insulative but thermally conductive layer may be a thin coating of one or more materials such as thermal pyrolytic graphite, graphite, graphene, diamond, diamond-like carbon (DLC) coatings, alumina, sapphire, zirconia, tantala, titania, beryllium oxide, polymer composites containing thermally conductive particles, nanoparticles, self-assembling nanoparticles, nanomaterials and composites, biocompatible thermally conductive fluids like olive oil, medical grade silicone oil, and similar materials. Further, this layer may be between approximately 10 nm and approximately 5000 nm.

Alternatively, the electrodes 30 may be integral to the carrier arm 90, with the conductive regions 70 being exposed or not having an outer oxide layer or layer of electrically insulated but thermally conductive material (for example, diamond-like carbon). In either configuration, the non-tissue-facing surfaces of both the electrode 30 and the carrier arm 90 (for example, if the carrier arm 90 is selectively conductive) may include an electrically isolated but thermally conductive layer, with only the anterior or tissue-facing surfaces of the electrodes 30 being conductive. Further, in all embodiments, the conductive regions 70 may be smaller than the non-conductive or selectively conductive portions, or they may be the same size. None of the figures shown herein may be drawn to scale. FIGS. 10C-10H also show a portion of an enhanced electrogram signal (inset) that may be achieved using the devices of FIGS. 10C-10H.

Figure 10G:
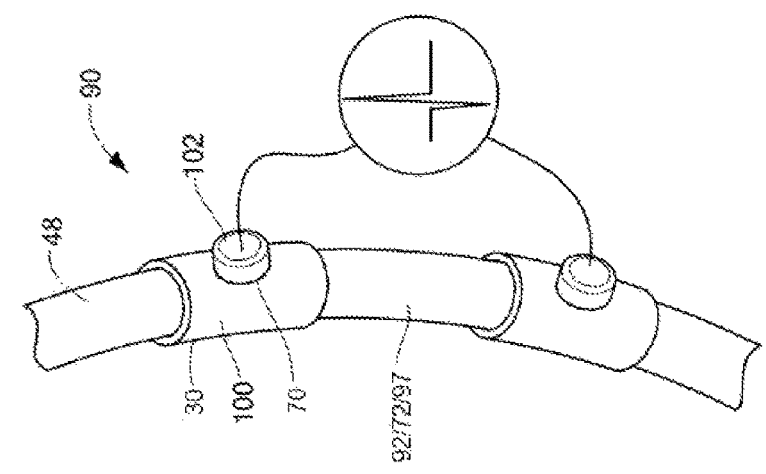

In FIGS. 10C-10E, the conductive regions 70 of the electrodes 30 may be linear. In FIGS. 10E-10H, the conductive regions 70 may be substantially circular. In FIGS. 10G and 10H, the circular conductive regions 70 may be raised or may protrude from the surface of the carrier arm 90 in a prominent bump 102. As discussed in FIGS. 9B and 9C, this prominent bump 102 may further enhance electrogram signal quality. Further, when very minimal or open signal filtering is applied (for example, approximately 0.5 Hz to approximately 1000 Hz), the prominent bump 102 may produce a monophasic action potential when referenced against a non-tissue-facing reference electrode 24, as shown in FIG. 10H. The reference electrode 24 may be located on the distal portion of the elongate body 17 (as shown in FIG. 10A) or on a non-tissue-facing surface of the carrier arm 90 (not shown).

Figure 11:
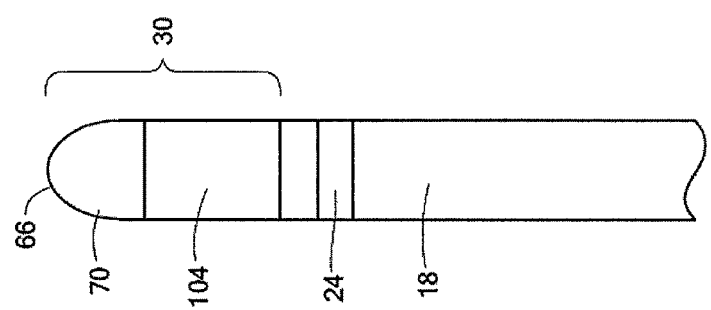
FIG. 11 shows an eleventh embodiment of a distal assembly.

Referring now to FIG. 11, an eleventh embodiment of a distal assembly is shown. The device may be a focal catheter having a rounded distal tip 66. A mapping and ablation electrode 30 may be disposed over the distal tip 66 and portion of the distal portion 22 of the elongate body 18, as shown. The electrode 30 may include a conductive region 70 and a non-conductive or selectively conductive region 104. In one configuration, the region 104 may be selectively conductive. Both the conductive 70 and selectively conductive 104 regions may be composed of a metal such as gold or gold alloy, and the selectively conductive region 104 may, for example, have a thin film layer of tantalum over the gold and the tantalum layer may be oxidized to tantalum pentoxide. As a non-limiting example, the oxide layer may be between approximately 10 nm to approximately 5000 nm, preferably approximately 100 nm to approximately 1000 nm. In this case, the conductive region 70 may be used for mapping procedures and the entire electrode 30 may be used for ablation or electroporation procedures (as described in more detail in, for example, FIG. 2). In another configuration, the region 104 may be non-conductive. The entire electrode 30 may be composed of a conductive metal (for example, gold or gold alloys), but the non-conductive region 104 may have a coating with a material that is highly thermally conductive but is fully electrically insulative, such as thermal pyrolytic graphite, graphite, graphene, diamond, diamond-like carbon (DLC) coatings, alumina, sapphire, zirconia, tantala, titania, beryllium oxide, polymer composites containing thermally conductive particles, nanoparticles, self-assembling nanoparticles, nanomaterials and composites, biocompatible thermally conductive fluids like olive oil, medical grade silicone oil, and similar materials. In this case, the device may provide enhanced electrogram signal quality (due to the smaller region of the electrode 30 that is used for mapping procedures and the interference-mitigating effect of the coating), a high cooling capability, and a reduced loss of ablation or electroporation energy to the bloodstream.

Figure 12A:
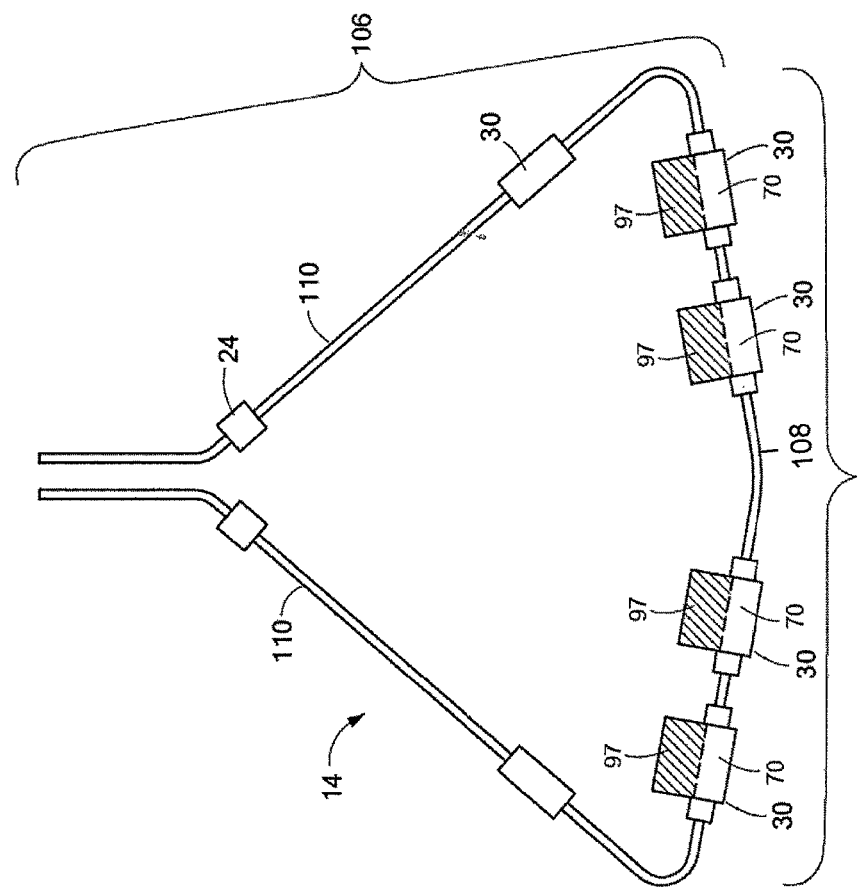
FIG. 12A shows a twelfth embodiment of a distal assembly.
Figure 12B:
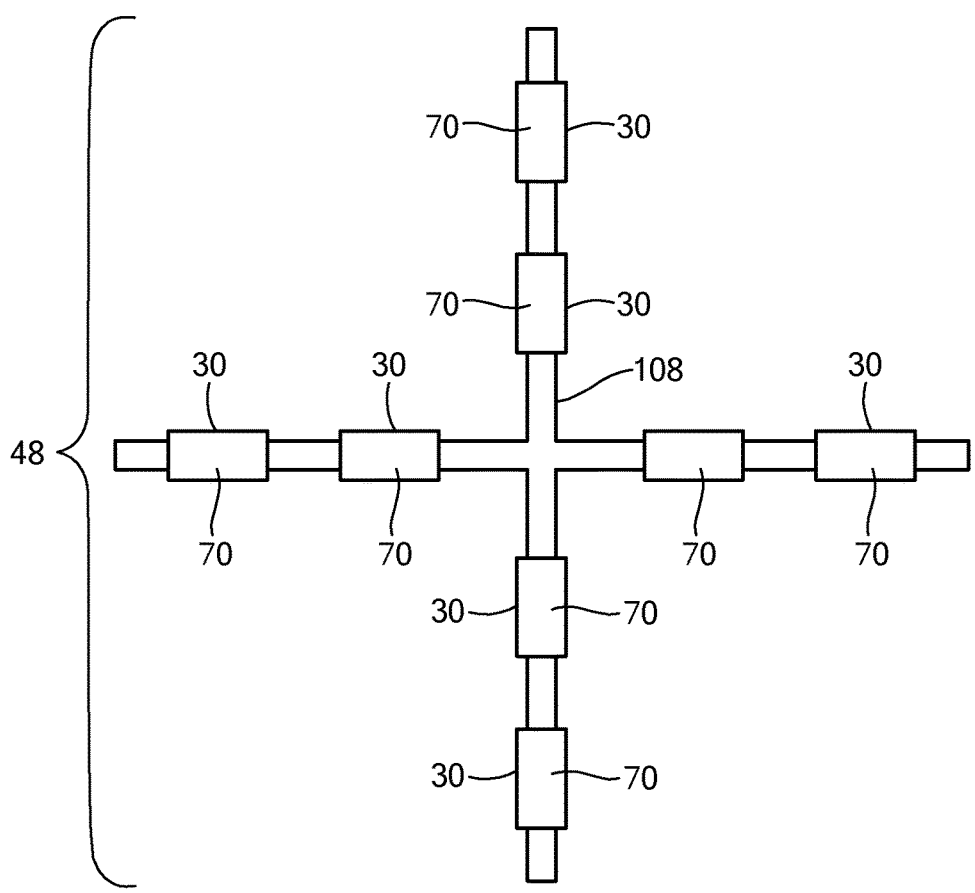
FIG. 12B shows a view of the anterior face of an embodiment of the distal assembly of FIG. 12A.

Referring now to FIGS. 12A and 12B, a twelfth embodiment of a distal assembly is shown. The distal assembly 14 may include one or more carrier arms 106 bearing one or more mapping and/or ablation electrodes 30. One carrier arm 106 is shown in FIG. 12A for simplicity; however, two or more carrier arms 106 may be used. For example, FIG. 12B shows the anterior or tissue-facing surface 48 of distal assembly 14 including two carrier arms 106. Each carrier arm 106 may include a first portion 108 at the anterior or tissue-facing surface 48 of the carrier arm 106 on which the one or more mapping and/or ablation electrodes 30 are borne, and two second portions 110 that are coupled to the device 12. The distal assembly 14 may further include one or more reference electrodes 24. Each of the electrodes 30 may include a conductive region 70 and a region that is electrically insulated but highly thermally conductive 97. For example, both the conductive region 70 and the insulated region 97 may be composed of gold or gold alloy, whereas the insulated region 97 may include a thin film coating or layer of a material such as diamond-like carbon (DLC). Although not shown in FIG. 12A or 12B, the electrode 30 may be composed of gold with a thin film surface of tantalum, and may include selectively conductive regions 72 in which the tantalum layer is oxidized to form tantalum pentoxide. These selectively conductive regions 72 may largely correspond to the insulated regions 97 shown in FIGS. 12A and 12B. As a non-limiting example, the oxide layer may be between approximately 10 nm to approximately 5000 nm, preferably approximately 100 nm to approximately 1000 nm.

The point at which the first 108 and second 110 portion of each carrier arm 106 meet may form an acute angle. The second portion 110 of each arm 106 may be affixed to a shaft that is slidably movable within the elongate body 16 of the device 12, or affixed directly to the elongate body 18. Further, the distal assembly 14 may be composed of a resilient and deformable material, and may assume a first position for delivery (not shown) and a second position for mapping and/or treatment (as shown in FIG. 12A). When in the second expanded position, the first portion 108 of each arm 106 may lie in a plane that is substantially orthogonal to the longitudinal axis of the device 12. Still further, the resilient and deformable material may be biased toward either the first or second position and may be steerable by one or more pull wires, guide wires, rods, or other steering mechanisms controllable at or proximal to the handle 28 of the device 12. The one or more electrodes 30 may be capable of transmitting both low-frequency and high-frequency current, and may be suited for mapping, ablation, and/or electroporation.

Figure 10F:
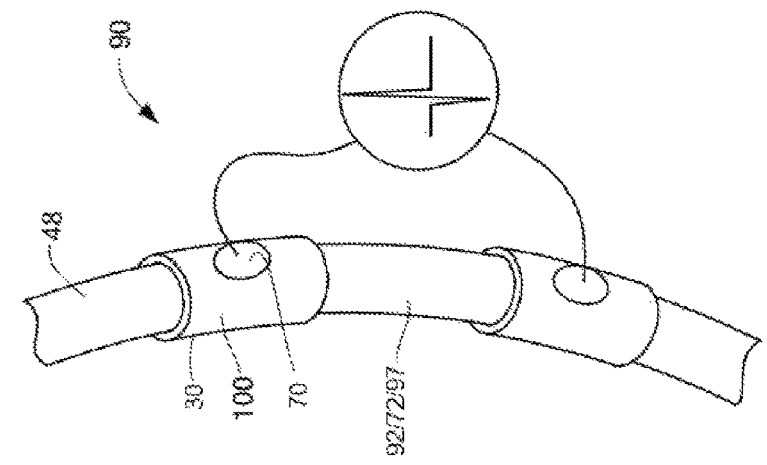

The embodiments shown and described in FIGS. 10 and 12, in particular, may be suited for anatomical placement, such that certain areas of the electrode 30 will be tissue contacting while other areas will only be in contact with the blood. The Medtronic Ablation Frontiers Pulmonary Vein Ablation Catheter® (PVAC) is an example of such a device as shown and described in FIGS. 10A-10H, and the Medtronic Ablation Frontiers Multi-Array Ablation Catheter® (MAAC) is an example of such a device as shown and described in FIGS. 12A and 12B. The exposed fully electrically conductive regions 70 of the electrodes 30 are specifically placed in areas of the electrode 30 that will contact cardiac muscle that is to be electrically mapped and potentially ablated. In some embodiments, the non-cardiac muscle facing portions of the electrode 30 may be coated with the electrically insulative material that is also highly thermally conductive. Two important functions are served by the coating: during mapping, the non-cardiac muscle (tissue) facing surfaces do not collect far-field electrical signals that degrade quality of local electrograms; and, during ablation (for example, RF ablation) or electroporation, the non-muscle facing surfaces do not waste energy to the blood but these surfaces serve to dissipate heat collected by the tissue facing side of the electrode, through the electrode and into the flowing blood.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:
1. A medical device comprising:
an elongate body; and
a distal assembly affixed to the elongate body and including a plurality of electrodes, each of the plurality of electrodes having a first region that is fully conductive and a second region that is one of selectively conductive and electrically insulated but thermally conductive, the second region including a first portion that includes a tissue-facing surface and a second portion opposite the first portion, the first region protruding from the tissue-facing surface of the first portion of the second region.

2. The device of claim 1, wherein the plurality of electrodes is composed of metal, the metal being at least one of platinum, platinum alloys, gold, gold alloys, gold with a coating of tantalum, copper with a coating of tantalum, copper with a coating of gold, aluminum, tungsten, titanium, tantalum, hafnium, niobium, zirconium, and combinations thereof.

3. The device of claim 1, wherein the second region is selectively conductive.

4. The device of claim 3, wherein the second region includes an oxide layer on an outer surface of the second region.

5. The device of claim 4, wherein the second region is composed of gold and the oxide layer is a layer of tantalum pentoxide.

6. The device of claim 4, wherein the second region is composed of copper and the oxide layer is a layer of tantalum pentoxide.

7. The device of claim 3, wherein the second region is configured to be conductive of at least one of high-frequency currents and pulsed energy, but is non-conductive of at least one of direct current energy and low-frequency currents.

8. The device of claim 1, wherein the second region is electrically insulated but thermally conductive.

9. The device of claim 8, wherein the second region includes a layer of diamond-like carbon on an outer surface of the second region.

10. The device of claim 8, wherein the second region includes a layer of at least one of thermal pyrolytic graphite, graphite, graphene, diamond, diamond-like carbon (DLC) coatings, alumina, sapphire, zirconia, tantala, titania, beryllium oxide, polymer composites containing thermally conductive particles, nanoparticles, self-assembling nanoparticles, nanomaterials, composites of nanomaterials, and biocompatible thermally conductive fluid on an outer surface of the second region.

11. The device of claim 10, wherein the second region includes a layer of biocompatible thermally conductive fluid on the outer surface of the second region, the biocompatible thermally conductive fluid being at least one of olive oil and medical grade silicone oil.

12. The device of claim 10, wherein the layer has a thickness of between approximately 10 nm and approximately 5000 nm.

13. The device of claim 1, wherein the second region is larger than the first region.

14. The device of claim 13, wherein the first region is configured to receive electrogram signals from tissue.

15. A medical device comprising:
an elongate body defining a distal portion, a proximal portion, and a longitudinal axis; and
an assembly affixed to the distal portion of the elongate body, the assembly including:
a carrier arm and being configured to transition between a first configuration and an expanded arcuate second configuration, the carrier arm having an anterior face that defines a distal plane that is substantially orthogonal to the longitudinal axis of the elongate body when the assembly is in the expanded second configuration; and
a plurality of electrodes coupled to the carrier arm, each of the plurality of electrodes having a first region and a second region, the first region being fully conductive and on the anterior face of the carrier arm when the carrier arm is in the expanded arcuate second configuration, the second region being one of selectively conductive and electrically insulated but thermally conductive, the first region being smaller than the second region and protruding beyond the distal plane of the anterior face from at least a portion of the second region.

16. The medical device of claim 15, wherein each of the plurality of electrodes is composed of metal, the metal being at least one of platinum, platinum alloys, gold, gold alloys, gold with a coating of tantalum, copper with a coating of tantalum, copper with a coating of gold, aluminum, tungsten, titanium, tantalum, hafnium, niobium, zirconium, and combinations thereof.

17. The medical device of claim 15, wherein the second region is selectively conductive and includes an oxide layer on an outer surface of the second region, the second region being configured to be conductive of at least one of high-frequency currents and pulsed energy, but is non-conductive of at least one of direct current energy and low-frequency currents.

18. The medical device of claim 15, wherein the second region is electrically insulated but thermally conductive, the second region including a layer of at least one of thermal pyrolytic graphite, graphite, graphene, diamond, diamond-like carbon (DLC) coatings, alumina, sapphire, zirconia, tantala, titania, beryllium oxide, polymer composites containing thermally conductive particles, nanoparticles, self-assembling nanoparticles, nanomaterials, composites of nanomaterials, and biocompatible thermally conductive fluid on an outer surface of the second region.

19. The medical device of claim 15, wherein the first region is configured to receive electrogram signals from tissue.

20. A medical device, comprising:
an elongate body defining a distal portion, a proximal portion, and a longitudinal axis; and
an assembly affixed to the distal portion of the elongate body, the assembly including:
a carrier arm and being configured to transition between a first configuration and an expanded second configuration, the carrier arm having an anterior face that defines a distal plane that is substantially orthogonal to the longitudinal axis of the elongate body when the assembly is in the expanded second configuration; and
a plurality of electrodes coupled to the carrier arm, each of the plurality of electrodes having a first region and a second region, the first region being fully conductive and on the anterior face of the carrier arm when the carrier arm is in the expanded second configuration, the second region being electrically insulated but thermally conductive, the first region being smaller than the second region and protruding beyond the distal plane of the anterior face from at least a portion of the second region, the first region being configured to receive electrogram signals from tissue, the second region including a layer of at least one of thermal pyrolytic graphite, graphite, graphene, diamond, diamond-like carbon (DLC) coatings, alumina, sapphire, zirconia, tantala, titania, beryllium oxide, polymer composites containing thermally conductive particles, nanoparticles, self-assembling nanoparticles, nanomaterials, composites of nanomaterials, and biocompatible thermally conductive fluid on an outer surface of the second region.

* * * * *